United States Patent [19]

Himmelmann et al.

[11] 4,043,818

[45] Aug. 23, 1977

[54] PROCESS FOR HARDENING PHOTOGRAPHIC LAYERS WITH CARBODIIMIDE COMPOUNDS CONTAINING SULPHOBETAINE GROUPS

[75] Inventors: Wolfgang Himmelmann, Opladen; Erwin Ranz, Leverkusen; Edy Roche, Cologne, all of Germany

[73] Assignee: AGFA-Gevaert, A.G., Leverkusen, Germany

[21] Appl. No.: 604,015

[22] Filed: Aug. 12, 1975

[30] Foreign Application Priority Data

Aug. 17, 1974 Germany .............................. 2439553

[51] Int. Cl.² ............................ G03C 1/40; G03C 1/30
[52] U.S. Cl. ..................................... 96/77; 96/111; 96/114; 96/76 R; 106/125; 260/117; 427/333; 427/338; 96/50 PT; 96/74; 96/67

[58] Field of Search ..................... 96/111, 114, 50 PT, 96/76 R, 77, 74, 72, 67; 260/117, 1; 106/125; 427/338, 333

[56] References Cited

U.S. PATENT DOCUMENTS 3,100,704  8/1963  Coles et al. ........................... 96/111

OTHER PUBLICATIONS

Robinson: Journal of Photographic Science, vol. 16, (1968), p. 41.

*Primary Examiner*—Won H. Louie, Jr.
*Attorney, Agent, or Firm*—Connolly and Hutz

[57] ABSTRACT

As quick-acting hardeners for protein-containing photographic layers, which do not adversely affect the sensitizers and color couplers in the photographic materials, carbodiimide compounds containing sulphobetaine groups are used.

9 Claims, No Drawings

PROCESS FOR HARDENING PHOTOGRAPHIC LAYERS WITH CARBODIIMIDE COMPOUNDS CONTAINING SULPHOBETAINE GROUPS

This invention relates to a process for hardening protein-containing, preferably gelatin-containing, photographic layers.

Numerous substances have already been described as hardening agents for proteins and, in particular, for gelatin. Substances of this kind include, for example, metal salts such as chromium, aluminium or zirconium salts, aldehydes and halogen-containing aldehyde compounds, more especially formaldehyde, dialdehydes and mucochloric acid, 1,2- and 1,4-diketones such as cyclohexane-1,2-dione and quinones, also chlorides of dibasic organic acids, the anhydrides of tetracarboxylic acids, compounds containing several reactive vinyl groups, such as vinyl groups, such as vinyl sulphones, acryl amides, compounds containing at least two readily splittable, heterocyclic 3-membered rings, such as ethylene oxide and ethylene imine, polyfuctional methane sulphonic acid esters and bis-$\alpha$-chloracyl amido compounds.

High molecular weight hardening agents, for example polyacrolein and its derivatives or copolymers and alginic acid derivatives, have recently become known, being used in particular as non-diffusing hardeners.

However, a number of serious disadvantages are involved in using the above-mentioned compounds for photographic purposes. Some of these compounds are photographically active and, for this reason, are unsuitable for hardening photographic materials, whilst others adversely affect the physical properties, for example the fragility, of the gelatin layers to such an extent that they cannot be used. Others of these compounds cause discoloration or produce a change in the pH-value during the hardening reaction. In addition, it is particularly important in hardening photographic layers that hardening should reach its maximum as soon as possible after drying so that the permeability to the developer solution of the material to be hardened does not continuously change, as is the case, for example, with mucochloric acid or formaldehyde.

In certain cases, crosslinking agents for gelatin also have a skin-harming effect, as is the case for example with the ethylene imine compounds, so that they cannot be used for physiological reasons alone.

It is also known that trichlorotriazine, hydroxy dichlorotriazine and dichloraminotriazines can be used as hardening agents. Disadvantages of these compounds include their relatively high vapour pressure, the precipitation of hydrochloric acid during hardening and the physiological effect of these compounds. Water-soluble derivatives, which contain carboxyl and sulphonic acid groups and which are obtained by reacting cyanuric chloride with 1 mol of a diaminoalkyl or diaminoaryl sulphonic acid or carboxylic acid, do not have any of these disadvantages and, for this reason, have recently been proposed for use as hardeners. However, there are limits to their suitability for use in practice because, on account of their high solubility, they decompose on standing in aqueous solutions and, as a result, quickly lose their activity. Finally, another important requirement which any hardener for photographic gelatin-containing layers has to satisfy, both for production and for processing reasons, is that it should also be possible to predetermine the onset of the crosslinking reaction within certain limits, for example by suitably selecting the drying temperature or by suitably selecting the pH-value.

Other known hardeners for photographic gelatin layers are compounds containing two or more acrylamido or vinyl sulphone groups in the molecule, for example divinyl sulphone, arylene-bis-vinyl sulphones and N,N',N''-tris-acryloyl-hydrotriazine or methylene-bis-vinyl sulphonamide.

Although the hardening effect of these compounds is good after a certain time, the compounds are substantially insoluble in water, which can lead to local irregularities in hardening within the layer.

The consequences of the undesirable properties of conventional hardeners as discussed above are extremely important in photography, because important photographic properties, such as gradation and sensitivity and, in many cases, silver covering power as well, are governed by the degree of crosslinking of the layer-forming colloid and change during storage. Although this disadvantage can be reduced by briefly aftertreating the hardened layer with ammonia or an amine, it cannot be eliminated altogether. Added to this is the fact that aliphatic divinyl sulphones harm the skin.

Carbodiimides have also long been used as hardeners for photographic materials. East German Patent Specification No. 7218 describes non-ionic carbodiimides as hardeners for photographic proteins. The iodides of carbodiimides containing amino groups are known from German Patent Specification No. 1,148,446, whilst toluene or methyl sulphonates are known from U.S. Patent Specification No. 3,100,704. Combinations of polymers containing carboxylic acids with gelatin and carbodiimides are mentioned in British Patent Specification No. 1,275,587.

The hardening of gelatin with 1-ethyl-3-dimethyl aminopropyl carbodiimide hydrochloride is described in the Article by Robinson in Journal of Photographic Science, Vol 16 (1968), page 41.

All carbodiimide compounds are suitable to a greater or lesser extent as quick-acting hardeners. However, they have disadvantages both from the photographic and from the toxicological point of view. The non-ionic carbodiimides, such as dicyclohexyl carbodiimide or diisopropyl carbodiimide, are substantially insoluble and harmful to the skin. The urea compounds formed during the reaction are precipitated in the layer and give rise to clouding. In addition, the more simple carbodiimides are known to be allergens. For use in practice, the carbodiimides have to be made water-soluble by the introduction of amino groups. The compounds containing amino groups are photographically active and still show some physiological activity. They reduce sensitivity after storage and increase photographic fogging in colour emulsions containing emulsified colour couplers. Finally, the water-soluble carbodiimides containing amino groups react with phenolic blue-green colour components to the detriment of the final colour densities.

The carbodiimides are known to react with phenols, thus preventing the coupling reaction in the case of Cyan dye forming components (F. Kurzer and K. Douraghl-Zadeh, Chem. Reviews, Vol. 67, No. 2, page 118 (1967)).

An object of the invention is to provide quick-acting hardeners for protein-containing photographic layers, more especially for gelatin-containing colour photographic layers, which have no harmful physiological effects and which do not adversely affect the sensitisers and colour components present in photographic materials.

Accordingly, the invention relates to a process for hardening protein-containing, more especially gelatin-containing, photographic layers which is distinguished by the fact that a carbodiimide containing a sulphobetaine group is used as a hardener.

The carbodiimides used in accordance with the invention correspond to the general formula:

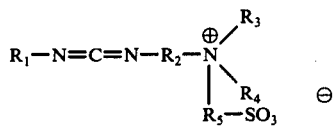

in which
- $R_1$ = alkyl with from 1 to 6 carbon atoms or cycloalkyl or alkoxy alkyl;
- $R_2$ = alkylene with from 2 to 4 carbon atoms;
- $R_3$ = alkyl with from 1 to 3 carbon atoms;
- $R_4$ = alkyl with from 1 to 3 carbon atoms or aryl, such as phenyl, or
- $R_3$ and $R_4$ together represent the atoms required to complete a 6-membered heterocyclic ring which, in addition to the N-atom, may also contain further hetero atoms, such as piperidine, piperazine or morpholine; and
- $R_5$ = alkylene with from 1 to 4 carbon atoms.

The following compounds are examples of preferred representatives of the hardeners used in accordance with the invention:

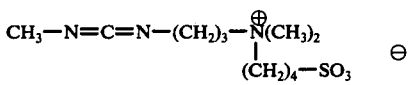

Compound 1

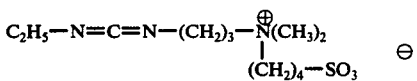

Compound 2

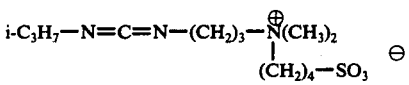

Compound 3

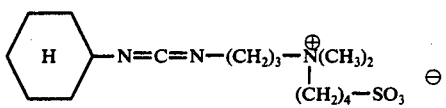

Compound 4

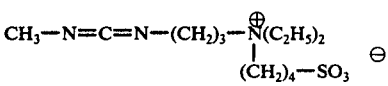

Compound 5

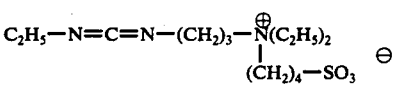

Compound 6

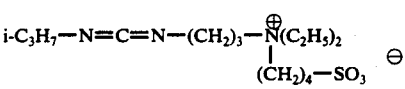

Compound 7

-continued

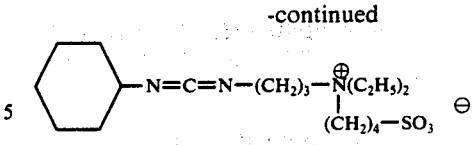

Compound 9

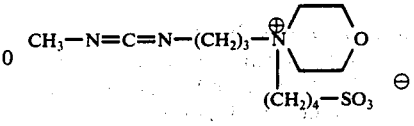

Compound 10

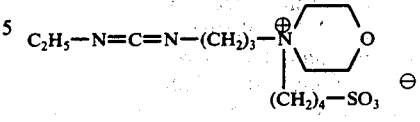

Compound 11

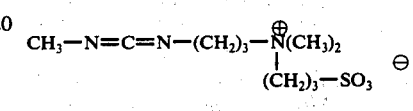

Compound 12

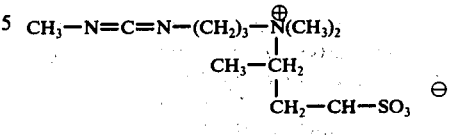

Compound 13

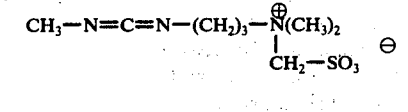

Compound 14

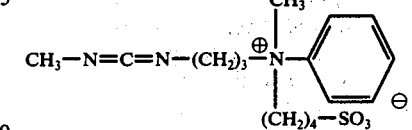

Compound 15

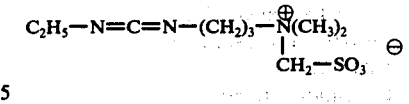

Compound 16

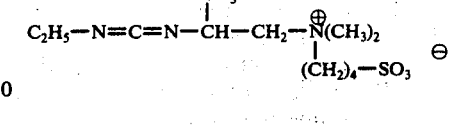

Compound 17

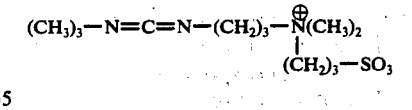

Compound 18

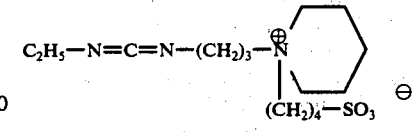

Compound 19

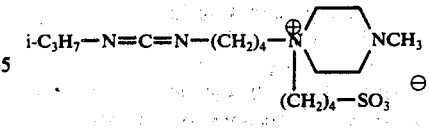

Compound 20

Compound 8

-continued

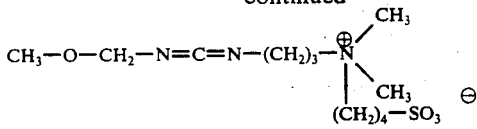

The compounds are new and are readily obtained from the carbodiimides containing amino groups by reaction with butane sultone or with the corresponding halogen alkyl sulphonic acids. The preparation of the starting products (carbodiimides containing amino groups) is described in the following literature references:

Sheehan, et al. J.org. Chem. 26, page 2525 (1961)

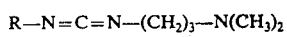

All the other starting derivatives may readily be obtained by these methods using corresponding substituted amines. Various starting materials are also commercially available products, such as 1-ethyl-3-dimethyl aminopropyl carbodiimide (OTT Chem. Company Muskegon, Michigan, or Ega-Chemie KG). The preparation of the compounds is also described in U.S. Patent Specifications Nos. 2,938,892 and 3,135,748.

The preparation of the compounds used in the invention is illustrated in the following Examples:

EXAMPLE 1

70.5 g of 1-methyl-3-(3-dimethyl aminopropyl)-carbodiimide, are dissolved in 150 ml of absolute dimethyl formamide, followed by the addition of 68 g of 1,4-butane sultone. After thorough mixing, the mixture is left standing for 3 to 4 days at room temperature. The crystal mass formed is stirred thoroughly with 100 ml of absolute acetone and then filtered under suction. The crystal mass is washed with absolute acetone.

After suspension in absolute acetone, the crystals are filtered off under suction, washed a few more times with absolute acetone and dried over calcium chloride in an desiccator.

Yield: 115 g, melting point: 135°–137° C.

The compound is analytically pure.

PREPARATION OF COMPOUND 2

77.5 g of 1-ethyl-3-(3-dimethyl aminopropyl)-carbodiimide are dissolved in 150 ml of absolute dimethyl formamide, followed by the addition of 68 g of 1,4-butane sultone. The clear mixture is left standing for 3 to 4 days at room temperature.

The crystal mass formed is thoroughly stirred with 100 ml of absolute acetone, filtered off under suction and washed with absolute acetone. The residue is stirred up in absolute acetone and filtered under suction (rewashing with acetone). The product is dried over calcium chloride in an exsiccator.

Yield: 95 g or 65% by weight of the theoretical yield.
Melting point: 141°–143° C.

The compound is analytically pure.

PREPARATION OF COMPOUND 12

15.2 g of sodium chloromethane sulphonate are dissolved in 180 ml of absolute dimethyl formamide, followed by the addition of 18.4 g of 1-ethyl-3-(3-dimethyl aminopropyl)-carbodiimide. This mixture is then stirred for 6 hours at 80° C in the absence of moisture. After cooling, the reaction product is precipitated by pouring the mixture into absolute ether. The crystallisate is filtered off under suction and washed thoroughly with absolute ether, followed by drying in an exsiccator.

Yield: 18 g. Melting point: 228°–230° C.

The product contains sodium chloride.

PREPARATION OF COMPOUND 4

27.2 g of butane sultone and 41.8 g of 1-cyclohexyl-3-(3-dimethyl aminopropyl)-carbodiimide are thoroughly mixed and left standing for 3 days at room temperature. The crystal mass formed is then stirred up with absolute acetone, followed by filtration under suction. The residue is washed with absolute acetone. It is suspended in absolute acetone, filtered off under suction and washed with absolute actone, as in the preceding preparations. The product is dried in an exsiccator.

Yield: 20 g. Melting point: 222°–224° C.

PREPARATION OF COMPOUND 6

13.6 g of butane sultone and 15.5 g of 1-ethyl-3-(3-diethyl aminopropyl)-carbodiimide are combined and, after thorough stirring, left standing for 3 days at room temperature. A brown viscous oil is deposited. It is separated off and rubbed a few times with absolute ether. It is dissolved in methylene chloride and precipitated in absolute acetone. The purification treatment is repeated a few times.

Yield: 6 g of a brown syrup.

PREPARATION OF COMPOUND 3

136 g of butane sultone and 152 g of 1-isopropyl-3-(3-dimethyl aminopropyl)-carbodiimide are combined and stirred for 6 hours in the absence of moisture. The mixture is then left standing for 2 to 3 days at room temperature. A solid mass is obtained. It is rubbed with absolute ether and filtered off under suction. The residue is resuspended in absolute acetone, filtered off under suction and washed with absolute water. The product is dried in an exsiccator.

Yield: 114 g. Melting point: 163°–165° C (highly hygroscopic).

The compound is analytically pure.

It was by no means foreseeable that the carbodiimides containing sulphobetaine groups would be stable either as prepared or in 100% pure form. It is known that the carbodiimides react with any groups containing active hydrogen atoms, such as for example carboxyl, amino or hydroxyl groups, sulphinic acid, phosphoric acid groups, phenols and thioalcohols. It is also known that sulphonic acids can be reacted with carbodiimides in benzene to form high yields of the anhydrides (Chem. Reviews, Vol. 67, No. 2 (1967), page 127).

The carbodiimides containing sulphobetaine groups according to the invention are eminently suitable for use as hardeners for gelatin layers of the kind containing additives emulsified in hydrophobic water-soluble droplets. The carbodiimides are not only hydrophilic, but are also strongly polar and, for this reason, are unable to migrate into the lipophilic particles.

By virtue of their betaine structure, the carbodiimides according to the invention have hardly any vapour pressure at room temperature. They are not volatile in water vapour and do not migrate into the air used for drying. As a result, they may be safely handled by personnel. The betaine structure also ensures that the hardener always remains in the aqueous phase (gelatin phase) at all pH-values. This distinguishes the carbodiimides according to the invention from all the conventional, basic carbodiimides for example 1-ethyl-3-(3-dimethyl aminopropyl)-carbodiimide.

The compounds used in accordance with the invention are best added to the protein layers to be hardened immediately before casting, preferably in the form of aqueous or alcoholic or aqueous-alcoholic solutions. Addition just before casting is necessary because the compounds react very quickly with gelatin or the other proteins normally used in photography. After the compounds have been added, the coating solutions should be cast within a few minutes. The velocity at which the hardening reaction takes place is governed primarily by the concentration of the proteins in the coating solution.

Another possibility is to cast the unhardened coating solutions and to coat the layers thus formed with a solution of the hardening compounds. It is also possible, however, to "bathe" the compounds, in the form of aqueous solutions containing sodium sulphate, into the unhardened or substantially unhardened photographic layers during processing of the photographic material, for example before development.

In the context of the invention, photographic layers are, in general terms, layers which are used in photographic materials, for example photosensitive silver halide emulsion layers, protective layers, filter layers, antihalo layers, backing layers or, quite generally, photographic auxiliary layers.

Photosensitive emulsion layers for which the hardening process according to the invention is particularly suitable are, for example, layers of the kind which are based on non-sensitised emulsions, orthochromatic, panchromatic, infrared emulsions, X-ray emulsions and other spectrally sensitised emulsions. The hardening process according to the invention has also proved to be suitable for hardening the gelatin layers used for the various black-and-white and colour photographic processes. The process according to the invention has proved to be particularly advantageous for hardening photographic layer combinations intended for carrying out colour photographic processes, for example layer combinations of the kind which contain emulsion layers with colour couplers, or emulsion layers intended for treatment with solutions containing colour couplers.

The effect of the compounds used in accordance with the invention is not in any way affected by the usual photographic additives. Similarly, the hardeners are non-reactive towards photographically active substances, such as water-soluble and emulsified water-insoluble colour components, stabilisers, sensitisers and the like. Nor do they have any effect upon the photosensitive silver halide emulsions. In addition, the compounds according to the invention may be combined with any of the compounds belonging to conventional classes of hardeners, for example with formalin, mucochloric acid, triacryl formal, bis-vinyl sulphones, bis-vinyl sulphonamides dialdehydes or bis-chloracetamides.

In addition to gelatin, the layers may contain water-soluble high polymers, more especially polyvinyl alcohol, sodium polyacrylate and other copolymers containing carboxyl groups, also polyvinyl pyrrolidone, polyacrylamide or high molecular weight naturally occurring substances, such as dextrans, dextrins, starch ethers, alginic acid and alginic acid derivatives.

The concentrations in which the hardeners according to the invention are used may fluctuate within wide limits and are essentially governed by the type of hardening compound used.

Good results have been obtained with quantities of from 0.1 to 10% by weight, preferably with quantities of from 0.2 to 8% by weight, based on the dry weight of the binder.

As already mentioned, the hardening reaction between the compounds according to the invention and the gelatin or proteins begins immediately, so that the optimum degree of hardening is obtained at substantially the same time as the layers are dried following casting and processing.

The effect of the hardening compounds is determined from the melting point of the layers, which may be determined as follows:

The layer cast onto a substrate is semi-immersed in water which is continuously heated at a temperature of up to 100° C. The temperature at which the layer runs off the substrate (streak formation) is referred to as the melting point or melting-off point. Pure protein or gelatin layers without hardeners do not show any increase in melting point whatever, as determined by this method. Under these conditions, the melting point is in the range of from 30° C to 35° C.

The compounds according to the invention surprisingly react quickly with proteins and, as a result, enable protein-containing materials to be quickly hardened to an optimum level. This unexpected effect of the compounds is of particular significance in the hardening of photographic materials containing proteins as binders. The required degree of hardening can be controllably adjusted during the preparation of the materials without any need for prolonged storage times and without the uncertainties of uncontrollable post-hardening which prolonged storage times involve.

The invention is illustrated by the following Examples in which all percentages are by weight unless otherwise stated.

EXAMPLE 1

Sodium sulphate is added almost to saturation concentration to 5% aqueous solutions of each of compounds 1, 2, 6, 10 and 15. Unhardened photographic silver halide gelatin layers are immersed for various periods in these solutions. The temperature amounts to 22° C. The layers are then briefly rinsed, dried and subsequently stored for 12 hours at room temperature. The effectiveness of these preliminary baths is determined from the melting points of the layers:

| Immersion time in minutes | Layer melting points in ° C | |
| --- | --- | --- |
| | Compound 1 | Compounds 2, 6, 10, 15 |
| 0.5 | 50° C | 60° C |
| 1 | 100° C | > 100° C |
| 2 | > 100° C | > 100° C |
| 3 | > 100° C | > 100° C |
| untreated layer 34° C | | |

At a bath temperature of 40° C, the immersion times required are much shorter and layer melting points above 100° C are obtained after only 45 seconds.

The stability of the auxiliaries according to the invention in aqueous solutions is governed by the type of additives used. In distilled water, they are still active after 3 days.

EXAMPLE 2

A 20% by weight zein solution is prepared in a mixture of ethanol and water (8:2), and is applied to the back of a cellulose acetate film. A layer which can readily be dissolved in a mixture of ethanol and water is obtained after drying.

If pieces of the film are bathed for 3 minutes in a solution of 2 g of compound 2, 1, 3, 4, 8, 13, 14, or 16
15 g of sodium sulphate
80 ml of water rinsed briefly with water and dried in a heating cabinet at 50° C to 60° C, the layer is insoluble in all solvents and effectively crosslinked.

EXAMPLE 3

An unhardened silver halide emulsion, containing 10% by weight of gelatin as binder, is coated onto a triacetyl cellulose substrate without the addition of a hardener. The layer otherwise contains all the usual additives. Samples of the dried layer are coated with 1%, 2% and 3% aqueous solutions of compounds 1, 2, 5, 13 and 16, followed by drying. The melting points, swelling values and set scratch resistances of the layers are then determined. The results are set out in Table 1.

The swelling values are gravimetrically determined after treatment of the layers for 10 minutes in distilled water at 22° C, and expressed in %.

To determine wet scratch resistance, a metal tip of defined size is drawn across the wet layer and placed under increasing weight. Wet scratch resistance is expressed by the weight under which the tip leaves a visible scratch on the layer. A high weight corresponds to a high wet scratch resistance and, hence, to effective hardening.

Table 1

| Compound | Layer melting point | Swelling in % | Wet scratch resistance in p |
|---|---|---|---|
| Compound 1 | | | |
| 1 % | | 320 | 750 |
| 2 % | 10'100°* | 280 | 750 |
| 3 % | | 250 | 1050 |
| Compound 2 | | | |
| 1 % | | 295 | 650 |
| 2 % | 10'100° | 260 | 850 |
| 3 % | | 235 | 1050 |
| Compound 5 | | | |
| 1 % | | 370 | 550 |
| 2 % | 10'100° | 280 | 850 |
| 3 % | | 260 | 900 |
| Compound 13 | | | |
| 1 % | | 320 | 650 |
| 2 % | 10'100°* | 280 | 850 |
| 3 % | | 250 | 950 |
| Compound 16 | | | |
| 1 % | | 320 | 850 |
| 2 % | 10'100° | 300 | 900 |
| 3 % | | 250 | 950 |
| not aftertreated: | 36° | 600–800 | 300 |

*The layer is still in place after 10 minutes in boiling water.

EXAMPLE 4

An unhardened silver halide emulsion, containing 10% by weight of gelatin, has added to it 20% by weight based on the gelatin, of a purple coupler corresponding to the following formula:

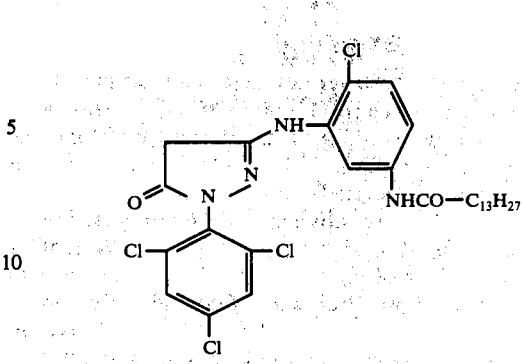

in emulsified form with the crystalloid dibutyl phthalate (1:1).

The usual casting additives apart from a hardener are then added to the emulsion. The mixture is cast onto a prepared substrate of polyethylene terephthalate, followed by drying.

Samples of this layer are then coated with 1 to 3% aqueous solutions of the compounds according to the invention. Layers with extremely high degrees of crosslinking are obtained after drying and storage for 10 hours. The results are shown in Table 2.

Table 2

| Coating | Melting point | Swelling in % | Wet scratch resistance in p |
|---|---|---|---|
| Compound 1 | | | |
| 1 % | | 310 | 450 |
| 2 % | 10'100° C | 280 | 550 |
| 3 % | | 260 | 650 |
| Compound 2 | | | |
| 1 % | | 295 | 550 |
| 2 % | 10'100° C | 260 | 650 |
| 3 % | | 235 | 750 |
| Compound 5 | | | |
| 1 % | | 320 | 450 |
| 2 % | 10'100° C | 270 | 550 |
| 3 % | | 250 | 650 |
| Compound 13 | | | |
| 1 % | | 410 | 450 |
| 2 % | 10'100° C | 350 | 550 |
| 3 % | | 300 | 600 |
| Compound 16 | | | |
| 1 % | | 380 | 500 |
| 2 % | 10'100° C | 320 | 550 |
| 3 % | | 280 | 650 |
| Compound 9 | | | |
| 1 % | | 410 | 450 |
| 2 % | 10'100° C | 350 | 500 |
| 3 % | | 300 | 550 |
| only treated with water | 42° C | 800 | — |

The photographic properties are not affected.

EXAMPLE 5

The usual additives apart from a hardener are added to 100 ml of a photographic silver bromide gelatin emulsion containing 10% by weight of gelatin. The mixture is coated a. onto a baryta paper,
b. onto paper lined with polyethylene on both sides.

After drying, samples of the two materials are bathed for 2 minutes in aqueous solutions of 3 g of each of compounds 1, 2, 5, 10, 11, 12, 13 and 14 in 100 ml of water. Layers unaffected by boiling (layer melting points 100° C) are obtained in every case after drying and storage for 12 hours. The hardening effect is not influenced in any way by the substrate. The non-aftertreated layers melt at 37° C.

EXAMPLE 6

An unhardened multilayer colour film consisting of
1. a 4 μ thick red-sensitive bottom layer containing per kg of emulsion 35 g of silver bromide, 80 g of gelatin and 24 g of $K_1$,
2. a μ thick intermediate layer of gelatin,
3. a 4 μ thick green-sensitive middle layer containing per kg of emulsion 35 g of silver bromide, 80 g of gelatin and 16 g of $K_2$,
4. a 2 μ thick yellow filter layer of colloidal silver in gelatin,
5. a 4 μ thick blue-sensitive top layer containing per kg of emulsion 35 g of silver bromide, 80 g of gelatin and 20 g of $K_3$, and
6. a 2 μ thick protective layer of gelatin, is cast in known manner onto a 120 μ thick layer substrate of cellulose triacetate, followed by drying. The film is then coated with 1% and 2% aqueous solutions of each of compounds 1, 2, 5, and 15.

The layer melting points and the layer separation temperatures are determined after drying and storage for 12 hours at room temperature.

| With coating | Layer Separation at | Layer melting point |
|---|---|---|
| Compound 2, | | |
| 1 % solution | > 100° C | 10'100° C |
| 2 % solution | > 100° C | 10'100° C |
| Compound 5, | | |
| 1 % solution | > 100° C | 10'100° C |
| 2 % solution | > 100° C | 10'100° C |

$K_1$

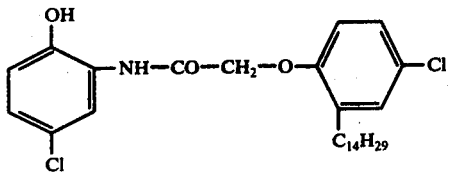

$K_2$

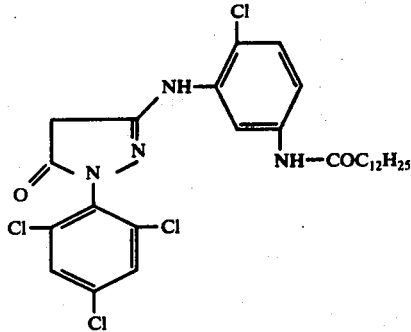

$K_3$

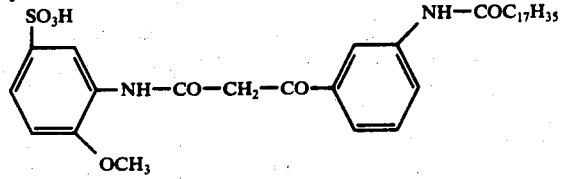

| With Coating | Layer Separation at | Layer melting point |
|---|---|---|
| Compound 16, | | |
| 1 % solution | 100° C | 10'100° C |
| 2 % solution | 100° C | 10'100° C |
| Compound 1, | | |
| 1 % solution | 100° C | 10'100° C |
| 2 % solution | 100° C | 10'100° C |

| | | |
|---|---|---|
| Comparison material not coated | 40° C | 40° C |

The results show that the multilayer colour films are effectively crosslinked by the coating through to the lowermost layers.

EXAMPLE 7

40 ml of a 5% aqueous solution of sodium polyacrylate and 10 ml of a 40% $SiO_2$-suspension are added to 100 ml of a 10% gelatin solution. The solution is thoroughly mixed. 0.2 g of each of compounds 2 and 6 are added to 100 ml batches of the solution, the pH-value is adjusted to 6.2 and the mixtures are subsequently cast onto a cellulose triacetate substrate. A layer with a melting point above 100° C, coupled with excellent wet scratch resistance, is obtained after drying and storage for 12 hours. A layer without any of the compounds according to the invention added to it melts in water at 40° C.

EXAMPLE 8

0.2 g of each of compounds 1 and 11 are added to 100 ml batches of a 10% aqueous solution of acetyl gelatin, obtained by reacting gelatin with 20% of acetanhydride, and the mixture is cast onto a cellulose acetate film. A layer containing 0.2 g of formalin instead of compounds 1 and 11 is used for comparison. Layers unaffected by boiling are obtained after drying with compounds 1 and 11. By contrast, the layers hardened with formalin melt below 100° C.

EXAMPLE 2

In order to demonstrate the advantages of the compounds according to the invention over conventional compounds, the following known compounds $V_1$ and $V_2$:

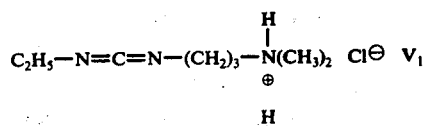

are compared with compounds 1, 2, 10, 11 and 15 according to the invention.

A cellulose triacetate substrate is coated with an unhardened silver halide emulsion containing 10% by weight of gelatin and 20% by weight of the phenolic cyan dye forming coupler:

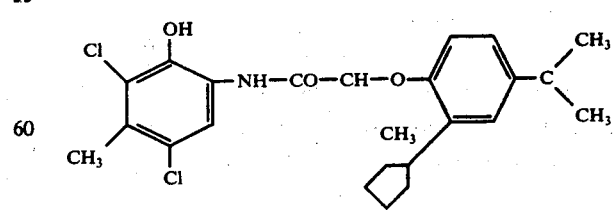

which has been emulsified into the casting composition together with 50% by weight (based on the coupler) of phthalic acid dibutyl ester. The usual additives apart from a hardener are then added to the emulsion.

These layers are then coated with aqueous solutions containing 1/100 mol/100 cm² of solution of each of compounds $V_1$, $V_2$, 1, 2, 10, 11 and 15.

The layers are exposed to light in a Densitometer and are subsequently processed under the same conditions in a colour development cycle.

The γ-values and the maximum densities of the individual samples are determined, the results being set out in Table 3.

Table 3

| Sample containing | F | KL | TR | $D_{MAX}$ F | KL | TR | Melting point | |
|---|---|---|---|---|---|---|---|---|
| $V_1$ | 1.40 | 1.40 | 1.90 | 1.36 | 1.53 | 1.70 | 100° C | |
| $V_2$ | 1.40 | 1.20 | 1.75 | 1.5 | 1.4 | 1.6 | 100° C | F = fresh sample |
| Compound 1 | 1.85 | 1.65 | 1.9 | 2.28 | 2.12 | 2.16 | 100° C | KL = conditioning cabinet (36 hours at 56° C/34 % relative air humidity) |
| Compound 2 | 1.75 | 1.75 | 1.81 | 2.05 | 2.15 | 2.18 | 100° C | |
| Compound 11 | 1.8 | 1.7 | 1.85 | 2.1 | 2.05 | 2.2 | 100° C | TR = tropical cabinet (storage for 3 days at 38° C/85 % relative air humidity) |
| Compound 12 | 1.75 | 1.6 | 1.75 | 2.0 | 2.1 | 2.1 | 100° C | |
| Compound 16 | 1.75 | 1.7 | 1.8 | 2.1 | 2.05 | 2.2 | 100° C | |

We claim:

1. The method of hardening a light sensitive photographic material comprising a silver halide emulsion layer and containing at least one supported layer containing protein by contacting the protein-containing layer with an effective amount of a hardener to harden the layer wherein the improvement comprises the hardener is an asymmetric carbodiimide compound of the following formula:

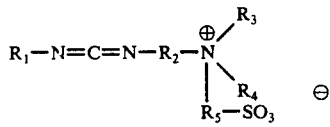

in which
$R_1$ = alkyl with from 1 to 6 carbon atoms or cycloalkyl or alkoxy alkyl;
$R_2$ = alkylene with from 2 to 4 carbon atoms;
$R_3$ = alkyl with from 1 to 3 carbon atoms;
$R_4$ = alkyl with from 1 to 3 carbon atoms or phenyl, or $R_3$ and $R_4$ together represent the atoms required to complete a 6-membered heterocyclic ring which, in addition to the N-atom, may also contain nitrogen or oxygen; and
$R_5$ = alkylene with from 1 to 4 carbon atoms.

2. Process according to claim 1 wherein the lightsensitive photographic material is a multilayered color photographic material.

3. A process as claimed in claim 1, wherein the protein-containing layer is selected from the group consisting of layers containing gelatin and carboxyl group-containing homopolymers and copolymers.

4. A process as claimed in claim 1, wherein the hardener is applied from an aqueous solution.

5. A process as claimed in claim 1, wherein the hardener is applied from an alcoholic solution.

6. A process as claimed in claim 1, wherein the hardener is applied from an aqueous-alcoholic solution.

7. A process as claimed in claim 1, wherein the hardener is used in quantities of from 0.2 to 8% by weight, based on the weight of a protein-containing binder, in a casting solution for the layer to be hardened.

8. A process as claimed in claim 1, wherein the hardener is used in the form of a 0.1 to 10% solution before processing of the photographic material.

9. A process as claimed in claim 1, wherein the layer to be hardened is coated with a 0.1 to 10% solution of the hardener and the layer is subsequently dried.

* * * * *